US012267931B2

(12) United States Patent
Jarboe et al.

(10) Patent No.: US 12,267,931 B2
(45) Date of Patent: Apr. 1, 2025

(54) CIRCADIAN EFFECTIVE LUMINAIRE

(71) Applicants: Charles Jarboe, Troy, NY (US); Andrew Bierman, Albany, NY (US); Mariana Gross Figueiro, Troy, NY (US); Mark S. Rea, Melrose, NY (US)

(72) Inventors: Charles Jarboe, Troy, NY (US); Andrew Bierman, Albany, NY (US); Mariana Gross Figueiro, Troy, NY (US); Mark S. Rea, Melrose, NY (US)

(73) Assignee: Rensselaer Polytechnic Institute, Troy, NY (US)

(*) Notice: Subject to any disclaimer, the term of this patent is extended or adjusted under 35 U.S.C. 154(b) by 0 days.

(21) Appl. No.: 18/277,811

(22) PCT Filed: Feb. 18, 2022

(86) PCT No.: PCT/US2022/016970
§ 371 (c)(1),
(2) Date: Aug. 18, 2023

(87) PCT Pub. No.: WO2022/178250
PCT Pub. Date: Aug. 25, 2022

(65) Prior Publication Data
US 2024/0314911 A1  Sep. 19, 2024

Related U.S. Application Data

(60) Provisional application No. 63/150,644, filed on Feb. 18, 2021.

(51) Int. Cl.
*H05B 47/16* (2020.01)
*F21S 6/00* (2006.01)
(Continued)

(52) U.S. Cl.
CPC .............. *H05B 47/16* (2020.01); *F21S 6/002* (2013.01); *F21S 6/008* (2013.01); *F21S 8/061* (2013.01);
(Continued)

(58) Field of Classification Search
CPC ........ F21S 6/002–008; F21S 8/02–068; F21V 1/00–24; F21V 23/0471; H05B 47/115
See application file for complete search history.

(56) References Cited

U.S. PATENT DOCUMENTS 9,827,440 B2   11/2017  Moore-Ede et al.
10,278,252 B2   4/2019  Li et al.
(Continued)

FOREIGN PATENT DOCUMENTS

WO   2020169383 A1   8/2020

OTHER PUBLICATIONS

International Search Report and The Written Opinion of the International Searching Authority, International Application No. PCT/US2022/016970, mailed Jun. 2, 2022.

*Primary Examiner* — Jason M Han
(74) *Attorney, Agent, or Firm* — Barclay Damon LLP; Anthony P. Gangemi (57) ABSTRACT

A luminaire includes a frame, an ambient light source positioned within the frame adjacent a first end of the frame, a downlight light source positioned within the frame adjacent a second end of the frame, a diffuser connected to the frame and at least partially surrounding the ambient light source, and a reflector configured to direct light emitted by the downlight light source. A first driver is in electrical communication with the ambient light source and is configured to adjust the illuminance of the ambient light source. A second driver is in electrical communication with the downlight light source and is configured to adjust the illuminance
(Continued)

of the downlight light source. A controller is in electrical communication with and send control signals to the drivers to change the light sources between a plurality of illuminance modes, which includes a circadian effective mode and a circadian ineffective mode.

20 Claims, 10 Drawing Sheets

(51) Int. Cl.
*F21S 8/06* (2006.01)
*F21V 1/04* (2006.01)
*F21V 23/04* (2006.01)
*F21Y 115/10* (2016.01)
*H05B 47/115* (2020.01)
*F21Y 113/20* (2016.01)

(52) U.S. Cl.
CPC ............ *F21V 1/04* (2013.01); *F21V 23/0471* (2013.01); *H05B 47/115* (2020.01); *F21Y 2113/20* (2016.08); *F21Y 2115/10* (2016.08)

(56) References Cited

U.S. PATENT DOCUMENTS

| | | |
|---|---|---|
| 2010/0142209 A1 | 6/2010 | Cuppett et al. |
| 2013/0258657 A1 | 10/2013 | Lin et al. |
| 2016/0273717 A1 | 9/2016 | Krames et al. |
| 2016/0377272 A1 | 12/2016 | Chen et al. |
| 2017/0051887 A1 | 2/2017 | Zeng et al. |
| 2017/0299128 A1 | 10/2017 | Katona et al. |
| 2018/0043130 A1 | 2/2018 | Moore-Ede et al. |
| 2018/0172227 A1 | 6/2018 | Soler et al. |
| 2020/0109830 A1 | 4/2020 | Ogg et al. |
| 2020/0187336 A1 | 6/2020 | Verberkt et al. |
| 2020/0260543 A1 | 8/2020 | Larson et al. |

CIRCADIAN EFFECTIVE LUMINAIRE

CROSS REFERENCE TO RELATED APPLICATION(S)

This application is a U.S. National Stage Application of, and claims the priority benefit of, International Patent Application No. PCT/US2022/016970, filed Feb. 18, 2022, which claims the priority benefit of U.S. Provisional Patent Application No. 63/150,644, filed Feb. 18, 2021, the contents of which is are incorporated by reference as if disclosed herein in their entireties.

FIELD

The present technology generally relates to the area of illumination, and more particularly, to devices and methods for providing circadian effective light sources.

BACKGROUND

Traditionally, luminaires for residential applications prioritize aesthetics and visual performance for common tasks such as cooking in the kitchen, washing up in the bathroom, and reading in the living room. It is generally the case that, given Illuminating Engineering Society ("IES") recommended horizontal illuminance levels for residential spaces, ambient light levels in the home are low compared to common commercial applications. Recent research has shown that light-besides enabling the performance of visual tasks—is the primary synchronizer of the human body's internal timing mechanism and is critically important for maintaining entrainment with the 24-hr light-dark cycle at one's local position on Earth. In the absence of this primary exogenous cue, or, conversely, in the presence of circadian stimulation at an inappropriate time of day (e.g., late in the evening), the circadian system can become disrupted, potentially leading to negative health outcomes such as metabolic and cardiovascular disease, some forms of cancer, sleep disruption, and various problems relating to mood and general health. Circadian entrainment requires light incident on the retina in sufficient amount and spectral content at the right time of day. Typical lighting in the home-especially in homes in northern latitudes where daylight is minimal or non-existent for significant portions of the year—is often inadequate in this respect.

In residential spaces where higher light levels are needed for specific visual tasks such as cooking, the light is typically delivered from overhead from directional light sources such as recessed downlights, whereas luminaires designated to provide ambient illumination, with more potential to get light to the eye, tend to be more decorative in quality and offer relatively lower levels of light in a warm correlated color temperature ("CCT") in the 2700 to 3000 K range. General residential light levels—where 100 to 200 Lux on the horizontal working plane in a typical family room, informal dining, or breakfast area is common IES recommended practice-fall well below the illuminance required for effective circadian entrainment.

Although some currently available lighting products focus solely on health-related lighting products, or "smart LED lighting," of which circadian effect is but one of many advertised value added features, a common feature of these products is that they typically emit 500 to 800 lumens and are then often installed in light fixtures with shades that further reduce the light output, making the likelihood of receiving enough illuminance at the eye for daytime circadian stimulation from these products fairly low. Additionally, while these products can provide some circadian benefit if deployed strategically, they do not often come with guidelines for end-users as to how and when these products should be used, and what light settings should be programmed for what times of day, potentially leading to misuse.

What is needed, therefore, is a luminaire designed for use in residential applications that meets the requirements of circadian effectiveness in a low-glare, aesthetically pleasing way.

SUMMARY

According to an embodiment of the present technology, a luminaire is provided. The luminaire includes a frame, an ambient light source positioned within the frame adjacent a first end of the frame, a downlight light source positioned within the frame adjacent a second end of the frame, a diffuser connected to the frame and at least partially surrounding the ambient light source, and a reflector configured to direct light emitted by the downlight light source.

In some embodiments, the luminaire includes a first driver, a second driver, and a controller. The first driver is in electrical communication with the ambient light source and is configured to adjust the illuminance of the ambient light source. The second driver is in electrical communication with the downlight light source and is configured to adjust the illuminance of the downlight light source. The controller is in electrical communication with the first driver and the second driver. The controller is configured to send control signals to the first driver and the second driver to change the ambient light source and the downlight light source between a plurality of illuminance modes.

In some embodiments, the plurality of illuminance modes includes a circadian effective mode and a circadian ineffective mode.

In some embodiments, when operating in the circadian effective mode, the luminaire provides a circadian stimulus of at least 0.3, the illuminance of the ambient light source is at least 350 Lux, and the illuminance of the downlight light source is at least 300 Lux.

In some embodiments, when operating in the circadian ineffective mode, the luminaire provides a circadian stimulus of no more than 0.1, the illuminance of the ambient light source is no more than 50 Lux, and the illuminance of the downlight light source is at least 300 Lux.

In some embodiments, the controller is programmable and the luminaire includes a timeclock such that the controller automatically changes the luminaire between the circadian effective mode and the circadian ineffective mode at predetermined times.

In some embodiments, the plurality of illuminance modes includes an ambient-only mode and a downlight-only mode.

In some embodiments, the luminaire includes at least one occupancy sensor in communication with the controller. The at least one occupancy sensor is configured to detect occupants in a predetermined area near the luminaire and communicate occupancy data to the controller which, upon receiving the occupancy data, is configured to activate or deactivate the luminaire.

In some embodiments, the ambient light source includes at least one LED source and at least one lens, the at least one lens having approximately a 340-degree light distribution pattern.

In some embodiments, the ambient light source has a Lambertian light distribution pattern.

In some embodiments, the at least one LED source includes a plurality of concentric annular LED boards.

In some embodiments, the downlight light source includes an LED chip-on-board.

In some embodiments, the reflector is shaped such that the downlight light source has an asymmetric light distribution pattern.

In some embodiments, the asymmetric light distribution pattern includes an approximately 60-degree by approximately 110-degree pattern.

In some embodiments, the frame includes a plurality of perimeter members connecting the first end of the frame to the second end of the frame. The diffuser includes a plurality of panels, each of the plurality of panels is connected to and positioned between adjacent perimeter members of the frame.

In some embodiments, each of the plurality of perimeter members is curved such that the frame has a generally spherical shape.

In some embodiments, the frame includes an aperture at the second end of the frame. The reflector is positioned within the aperture.

In some embodiments, the reflector comprises a 3D printed material.

In some embodiments, the diffuser comprises a 3D printed material.

According to another embodiment of the present technology, a method of promoting circadian entrainment to an area is provided. The method includes the steps of: providing a lighting system including a luminaire and a controller in electrical communication with the luminaire, the luminaire including: a frame; an ambient light source positioned within the frame adjacent a first end of the frame; a downlight light source positioned within the frame adjacent a second end of the frame; a first driver in electrical communication with the ambient light source and the controller, the first driver is configured to adjust the illuminance of the ambient light source; a second driver in electrical communication with the downlight light source and the controller, the second driver is configured to adjust the illuminance of the downlight light source; a timeclock in electrical communication with the controller; a diffuser connected to the frame and at least partially surrounding the ambient light source; and a reflector configured to direct light emitted by the downlight light source; generating, via the timeclock, time of day data; communicating the time of day data to the controller; generating, via the controller, at least one illuminance mode control signal in response to the time of day data; communicating the at least one illuminance mode control signal to at least one of the first driver and the second driver; and adjusting the illuminance of at least one of the ambient light source and the downlight light source between a plurality of illuminance modes in response to the at least one illuminance mode control signal.

In some embodiments, the plurality of illuminance modes includes a circadian effective mode and a circadian ineffective mode.

In some embodiments, when operating in the circadian effective mode, the luminaire provides a circadian stimulus of at least 0.3, the illuminance of the ambient light source is at least 350 Lux, and the illuminance of the downlight light source is at least 300 Lux.

In some embodiments, wherein when operating in the circadian ineffective mode, the luminaire provides a circadian stimulus of no more than 0.1, the illuminance of the ambient light source is no more than 50 Lux, and the illuminance of the downlight light source is at least 300 Lux.

In some embodiments, the method further includes the steps of: detecting, via at least one occupancy sensor of the luminaire, occupants in a predetermined area near the luminaire; generating occupancy data; communicating the occupancy data to the controller; generating, via the controller, at least one of an activation or a deactivation control signal in response to the occupancy data; communicating the at least one of the activation or deactivation control signal to the first driver and the second driver; and adjusting the illuminance of the ambient light source and the downlight light source in response to the at least one of the activation or deactivation control signal.

Further objects, aspects, features, and embodiments of the present technology will be apparent from the drawing figures and below description.

DETAILED DESCRIPTION

Embodiments of the present technology offer significant benefits over the current commercially available products. The market for residential lighting products for circadian effect, or "human-centric lighting," primarily consists of spectrally tunable screw—in light bulbs for use in third-party light fixtures, or tabletop/desktop mounted luminaires for circadian stimulation intended to combat Seasonal Affective Disorder ("SAD") or to improve overall health and wellness. Currently available lighting products for at-home use may provide some circadian-effective illumination, but at the expense of high levels of discomfort glare. For example, SAD lamps and desktop luminaires often target exceedingly high light levels (about 10,000 Lux), often with relatively cool color temperatures in the 5000-6500 K range, and are relatively small in scale to fit comfortably on a desktop or kitchen counter, and as a result, can appear very bright and uncomfortably glaring.

The researchers of the present technology have determined that approximately 300 lux of a 3000 K light source is needed at the eye to provide an effective circadian stimulus ("CS") of at least 0.3-equivalent to 30 percent nocturnal melatonin suppression after a one-hour exposure to the light source. To promote entrainment, an occupant of the space should be exposed to a CS≥0.3 for at least 1-2 hours during the morning/daytime hours and a CS≤0.1 (below the threshold for a circadian response) during the evening/nighttime to avoid circadian disruption.

The present technology addresses several shortcomings of traditional lighting products commonly specified for residential applications when it comes to circadian effectiveness. First, the luminaire according to some embodiments provides adequate vertical illuminance (approximately 300 Lux) from a 3000 K LED light source to the eyes of occupants seated in the proximity of the luminaire. Second, the luminaire according to some embodiments is low glare and visually comfortable as a result of its scale, design, and the level and uniformity of the luminance of the light-diffusing material. Third, the luminaire according to some embodiments has an onboard timeclock enabling it to deliver a circadian effective light stimulus during the daytime hours, and a circadian ineffective light stimulus during the evening hours (when circadian stimulation should be avoided) while still providing enough horizontal illuminance for common visual tasks such as reading. Fourth, the luminaire according to some embodiments includes integral occupancy sensing capabilities to automatically turn on when an occupant of the space is seated near it and will be able to log a variety of parameters such as occupancy and energy data for research purposes.

Figure 1:
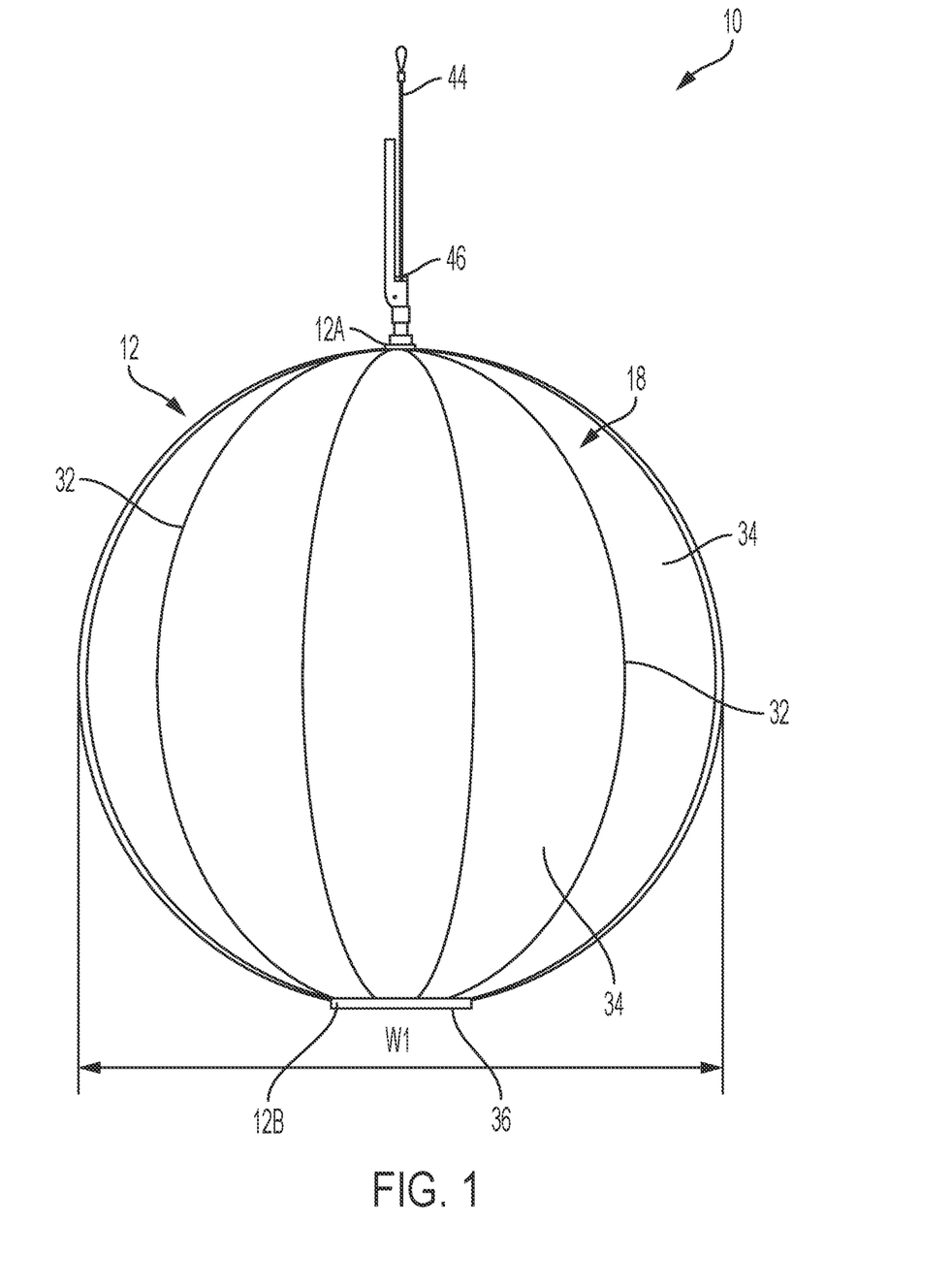
FIG. 1 is a side elevational view of an exemplary luminaire according to an embodiment of the present technology.
Figure 2:
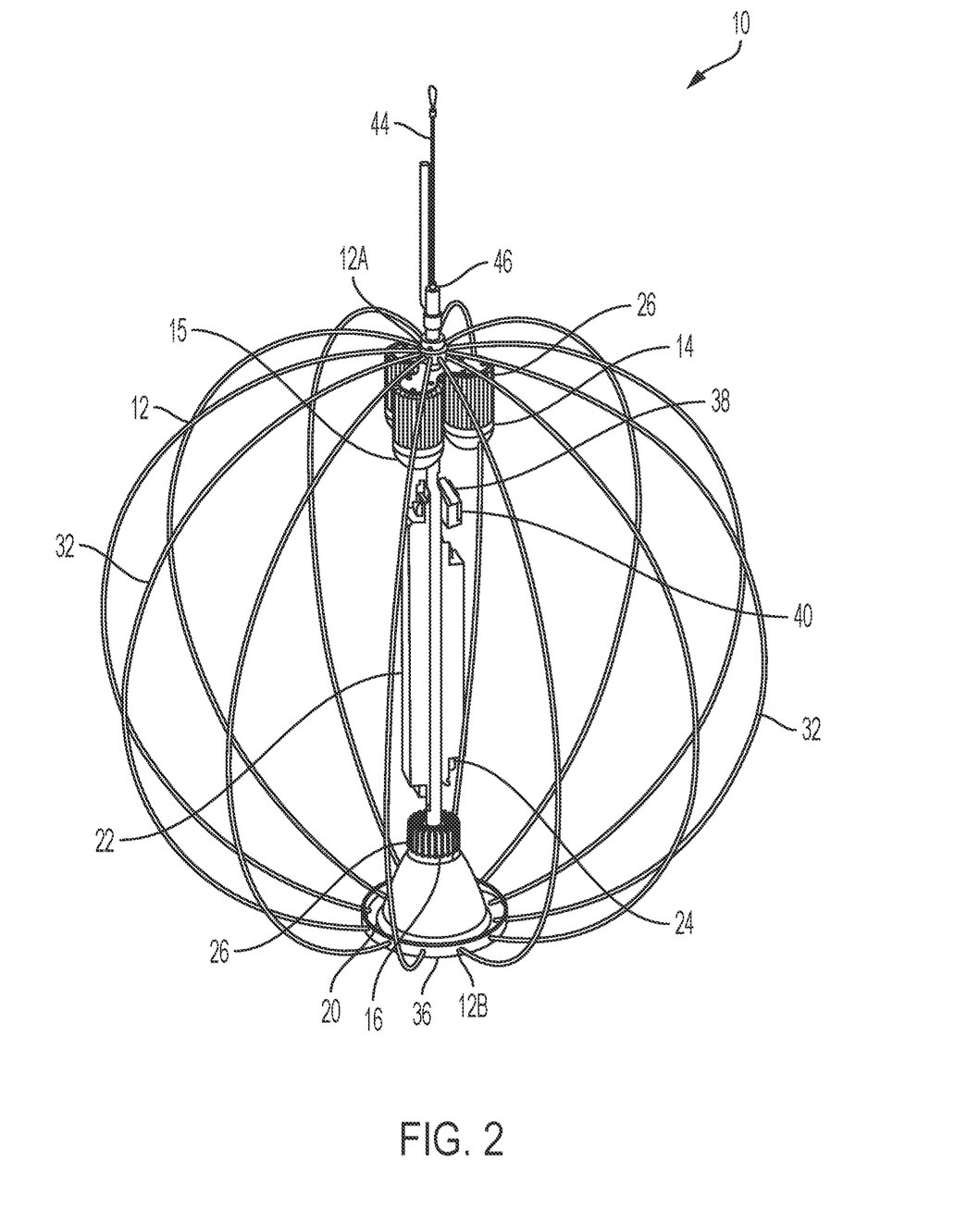
FIG. 2 is an isometric view of the luminaire of FIG. 1 shown without the diffuser assembled on the frame.

FIGS. 1-2 show a luminaire 10 according to an exemplary embodiment of the present technology. The luminaire 10 has a frame 12, an ambient light source 14 positioned within the frame 12 adjacent a first end 12A of the frame 12, and a downlight light source 16 positioned within the frame 12 adjacent a second end 12B of the frame 12. A diffuser 18 is connected to the frame 12 and at least partially surrounds the ambient light source 14. A reflector 20 is positioned within the frame 12 and is configured to direct light emitted by the downlight light source 16. The ambient light source 14 is in electrical communication with a first driver 22 that is configured to adjust the illuminance of the light emitted by the ambient light source 14. The downlight light source 16 is in electrical communication with a second driver 24 that is configured to adjust the illuminance of the light emitted by the downlight light source 16. In some embodiments, each of the ambient light source 14 and the downlight light source 16 is an LED source having a heat sink 26.

Figure 4A:
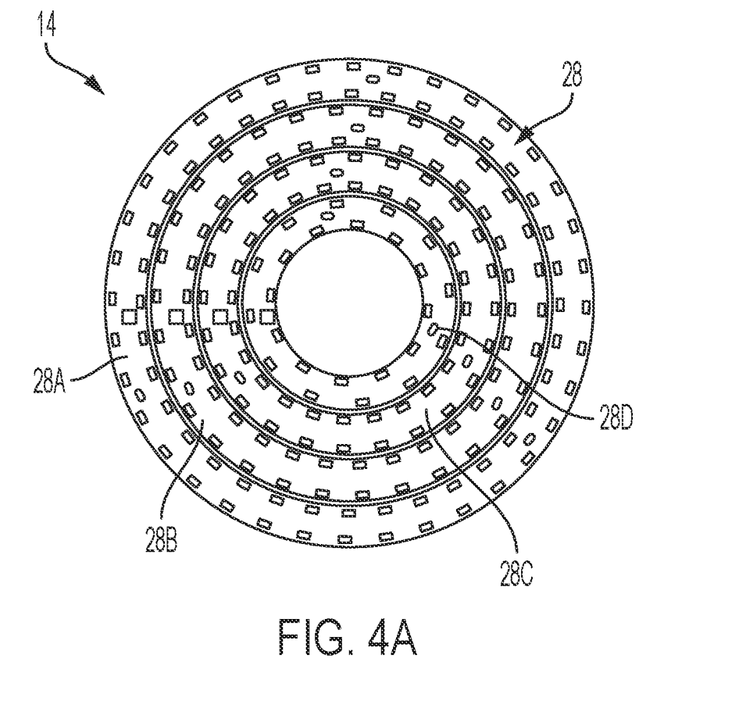
FIG. 4A is a plan view of an exemplary ambient light source according to an embodiment of the present technology.

In some embodiments, the ambient light source 14 includes a plurality of light sources. For example, the ambient light source 14 shown in FIG. 2 includes three light sources. However, the present technology is not limited thereto and contemplates embodiments where the ambient light source 14 has more or less than three light sources. In some embodiments, the ambient light source 14 includes a lens 15 with approximately a 340-degree distribution pattern that mimics a traditional light bulb beam pattern. In some embodiments, the ambient light source 14 has a Lambertian light distribution pattern. In some embodiments, the ambient light source 14 includes at least one annular LED board 28 having a lumen output of 8000 lm, a correlated color temperature ("CCT") of 3000 K, and a Lambertian distribution pattern. As shown in FIG. 4A, the at least one annular LED board 28 includes a plurality of concentric annular LED boards 28A, 28B, 28C, and 28D. However, the present technology is not limited thereto and contemplates embodiments where the annular LED board includes more or less than four concentric annular LED boards.

Figure 4B:
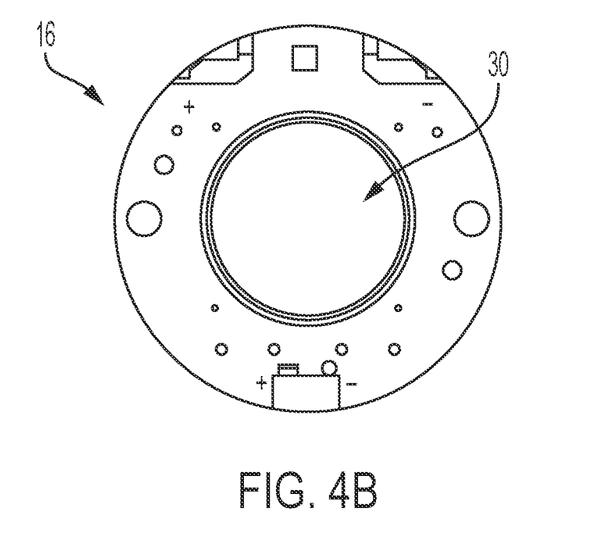
FIG. 4B is a plan view of an exemplary downlight light source according to an embodiment of the present technology.

In some embodiments, the downlight light source 16 includes an LED chip-on-board 30, as shown in FIG. 4B. In some embodiments, the LED chip-on-board 30 has a lumen output of 1000 lm and a CCT of 3000 K.

As shown in FIGS. 1-2, the frame 12 includes a plurality of perimeter members 32 connecting the first end 12A of the frame 12 to the second end 12B of the frame 12. In some embodiments, each of the plurality of perimeter members 32 is curved such that the frame 12 has a generally spherical shape. However, the present technology is not limited thereto and contemplates embodiments where the frame 12 has a different shape, including but not limited to ellipsoidal, cylindrical, hexagonal prism, octagonal prism, pyramidal, hourglass, etc.

Figure 10:
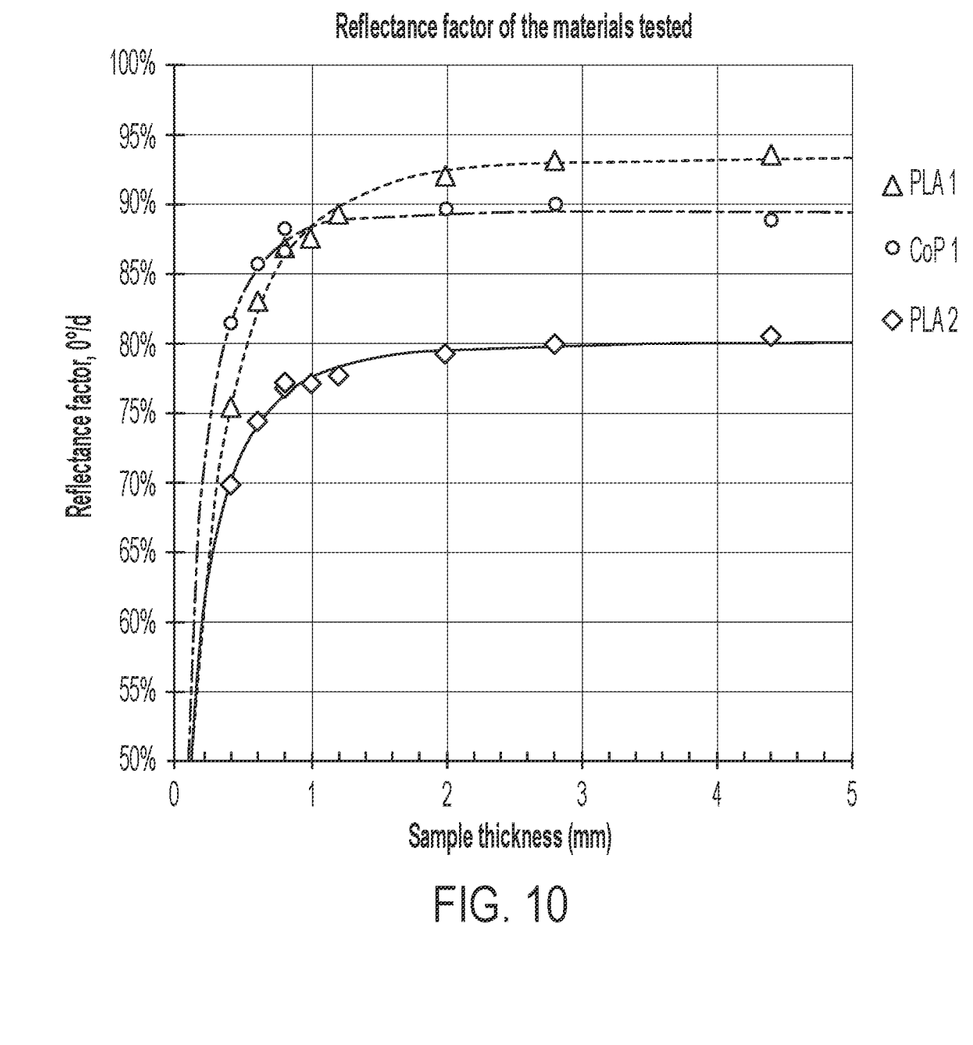
FIG. 10 is a chart showing the reflectance and transmittance properties of exemplary 3D printing materials.

As shown in FIGS. 1-2, the diffuser 18 is connected to the frame 12 at each of the plurality of perimeter members 32. In some embodiments, the diffuser 18 includes a plurality of panels 34, each of which are connected to and positioned between adjacent perimeter members 32 of the frame 12. In some embodiments, the diffuser 18 is one continuous piece. In some embodiments, the diffuser is formed of a translucent fabric. In some embodiments, the diffuser is formed of a 3D printed skin/mesh material, such as polylactic acid ("PLA"). In other embodiments, the diffuser is formed of a spray fiber on the frame, a molded plastic polymer, a stretched fabric on the frame, or any other suitable translucent material known in the art. FIG. 10 shows a chart that demonstrates the reflectance and transmittance properties of typical PLA 3D printing filaments, such as PLA 1, CoP 1, and PLA 2. The thinner the layer of material, the more light is transmitted (e.g., 30% for the thinnest material layer). For the material to be thin enough to transmit enough light, the printer must be capable of a high level of precision and printing resolution. Thus, the diffuser 18 is preferably printed in multiple panels 34 and assembled.

Figure 5:
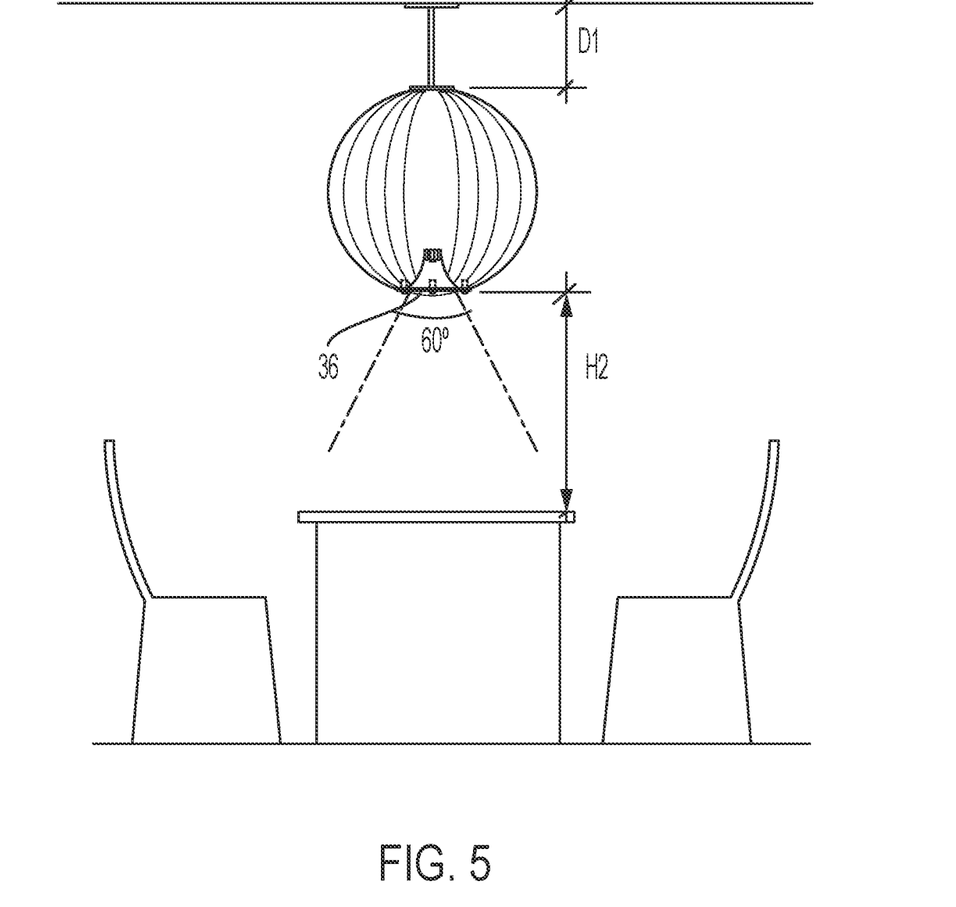
FIG. 5 is a side elevational view of an exemplary luminaire mounted to a ceiling and suspended above a table according to an embodiment of the present technology.
Figure 6:
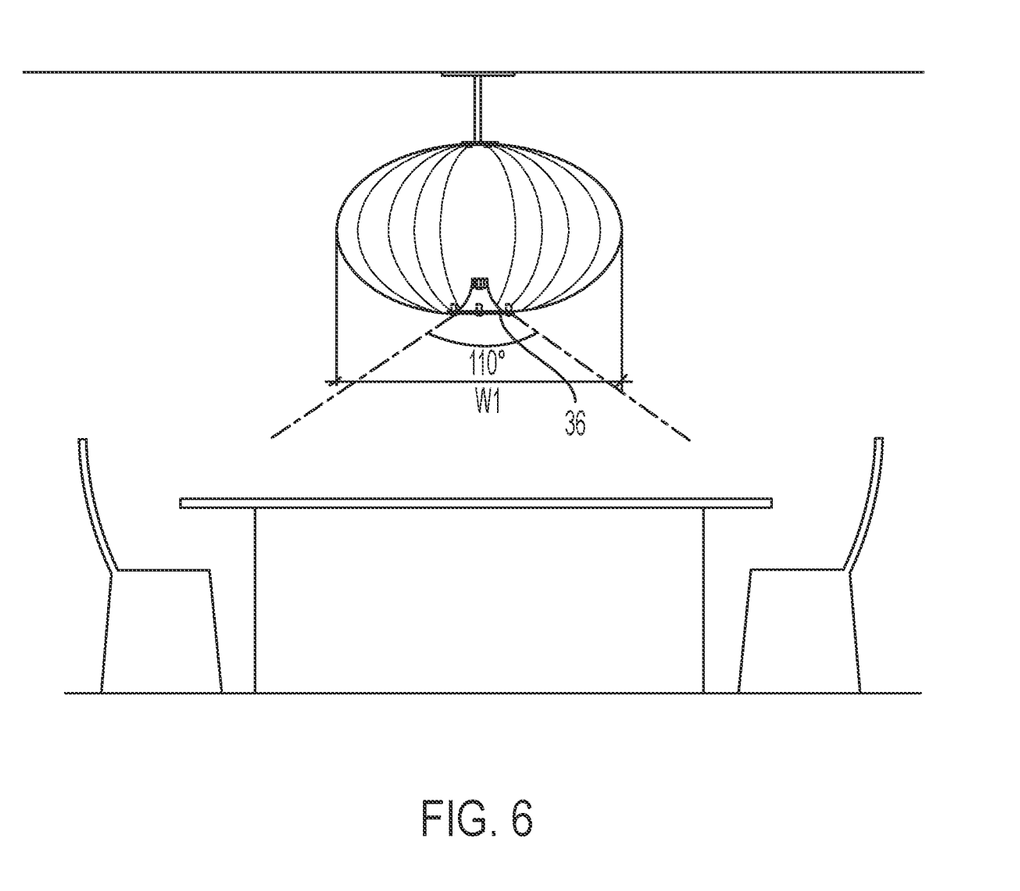
FIG. 6 is a side elevational view of an exemplary luminaire mounted to a ceiling and suspended above a table according to an embodiment of the present technology.

The frame 12 includes an aperture 36 at the second end 12B of the frame 12, as shown in FIG. 2. The reflector 20 is positioned within the aperture 36 such that the light emitted by the downlight light source 16 is focused by the reflector 20 through the aperture 36. In some embodiments, the reflector 20 is shaped such that the light emitted by the downlight light source 16 has an asymmetric light distribution pattern. In some embodiments, the asymmetric light distribution pattern is an approximately 60-degree by approximately 110-degree pattern, as shown in FIGS. 5-6. In some embodiments, the reflector 20 is formed of a 3D printed material, such as PLA.

In some embodiments, the luminaire 10 includes a controller 38 that is configured to adjust the illuminance of the luminaire 10. The controller 38 is in electrical communication with the first driver 22 and the second driver 24. The controller 38 generates control signals and communicates the control signals to the first driver 22 and the second driver 24 to change or adjust the illuminance of the ambient light source 14 and the downlight light source 16 between a plurality of illuminance modes. In some embodiments, the controller 38 is located within the luminaire 10, as shown in FIG. 2. In some embodiments, the controller 38 is located outside the luminaire 10 (e.g., mounted in a wall or in a remote control) such that the controller 38 and the luminaire 10 form a lighting system.

Figure 7:
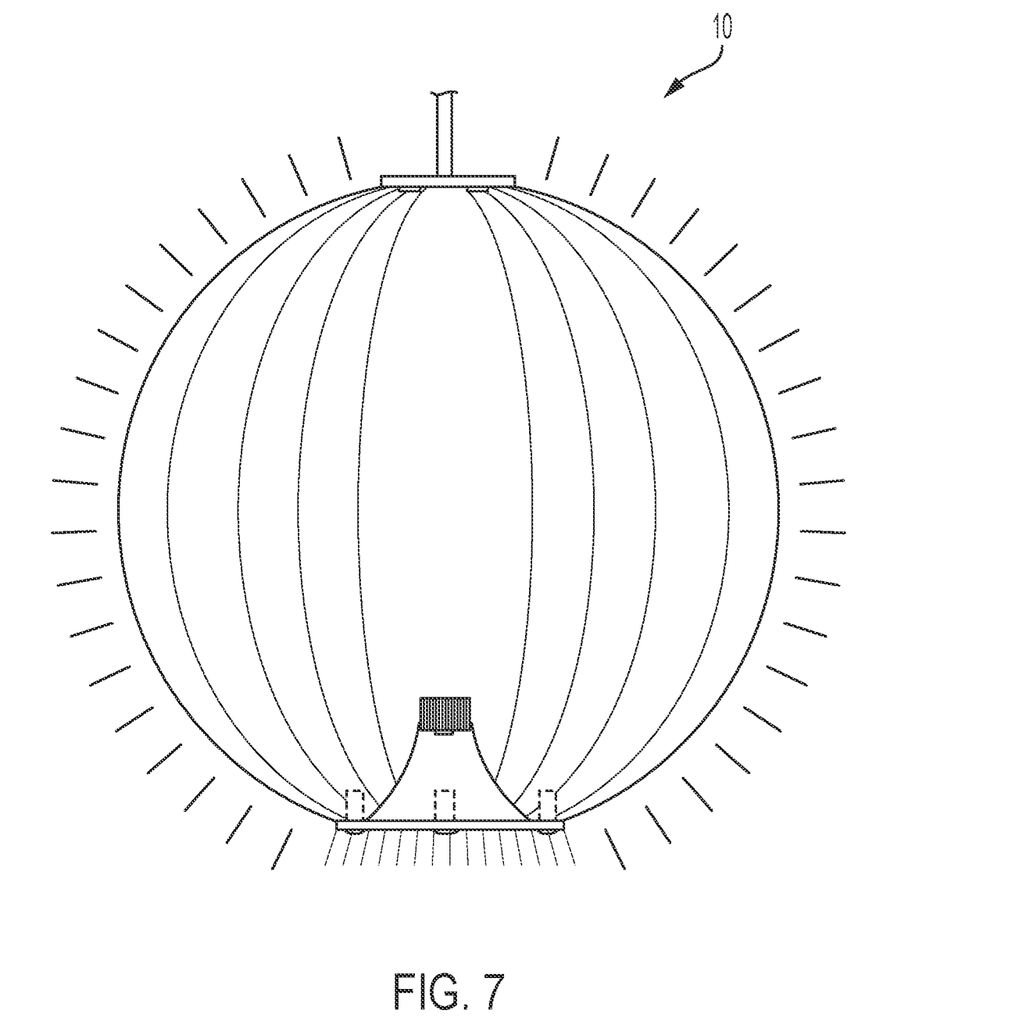
FIG. 7 is a side elevational view of an exemplary luminaire during operation of a circadian effective illumination mode according to an embodiment of the present technology.
Figure 8:
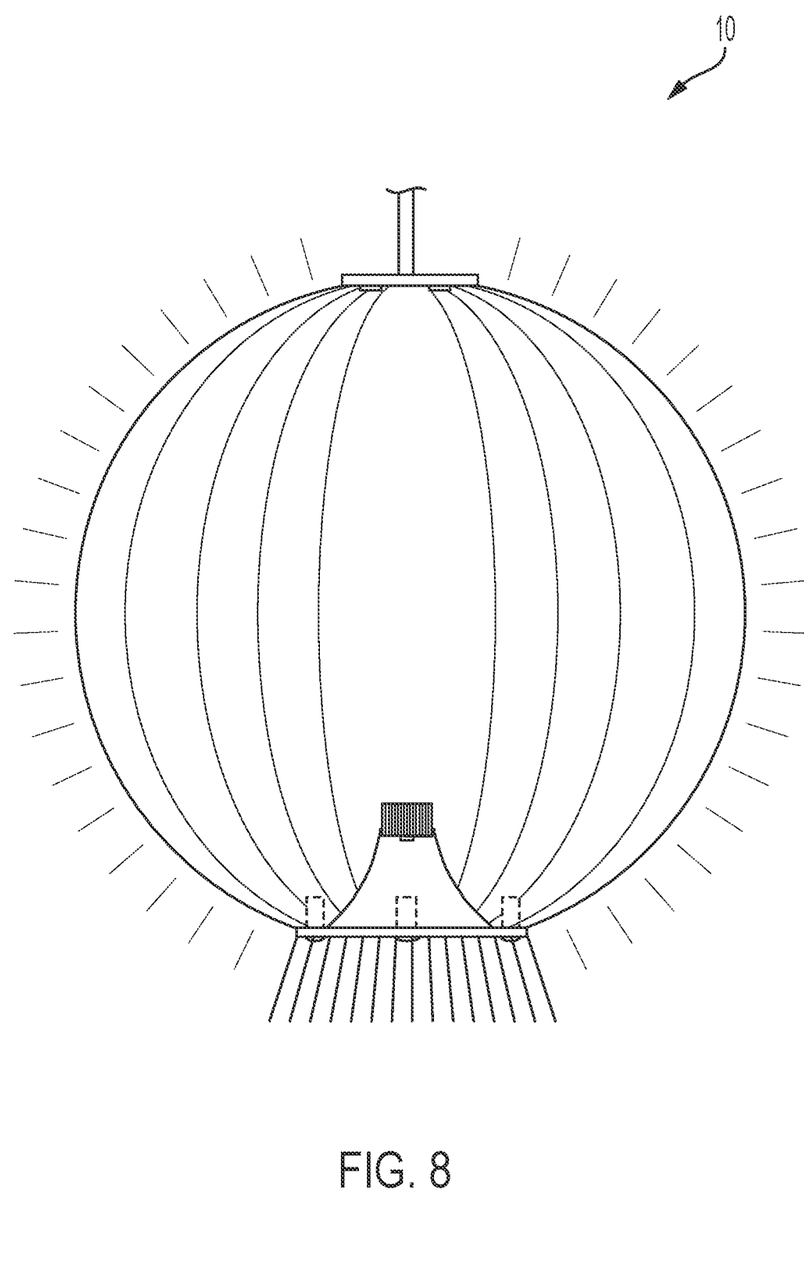
FIG. 8 is a side elevational view of an exemplary luminaire during operation of a circadian ineffective illumination mode according to an embodiment of the present technology.

The plurality of illuminance modes includes a circadian effective mode and a circadian ineffective mode. An exemplary operation of the luminaire 10 in the circadian effective mode (e.g., daytime mode) is shown in FIG. 7. When operating in the circadian effective mode, the luminaire 10 provides a circadian stimulus ("CS") of at least 0.3, the illuminance of the ambient light source 14 is at least 350 Lux, and the illuminance of the downlight light source is at least 300 Lux. An exemplary operation of the luminaire 10 in the circadian ineffective mode (e.g., evening or nighttime mode) is shown in FIG. 8. When operating in the circadian ineffective mode, the luminaire 10 provides a CS of no more than 0.1, the illuminance of the ambient light source 14 is no more than 50 Lux, and the illuminance of the downlight light source 16 is at least 300 Lux. In some embodiments, the plurality of illuminance modes includes an ambient-only mode (in which only the ambient light source 14 is active) and a downlight-only mode (in which only the downlight light source 16 is active).

As shown in FIG. 2, the luminaire 10, in some embodiments, includes an onboard timeclock 40 that is configured to track the time-of-day and generate time-of-day data for communication to the controller 38. Upon receiving the time-of-day data from the timeclock 40, the controller 38 automatically determines if the circadian effective illuminance mode or the circadian ineffective illuminance mode is required and, if necessary, generates and communicates control signals to the first driver 22 and the second driver 24 to change or adjust the ambient light source 14 and the downlight light source 16 between the illuminance modes. In some embodiments, the timeclock 40 is onboard the controller 38.

Figure 3:
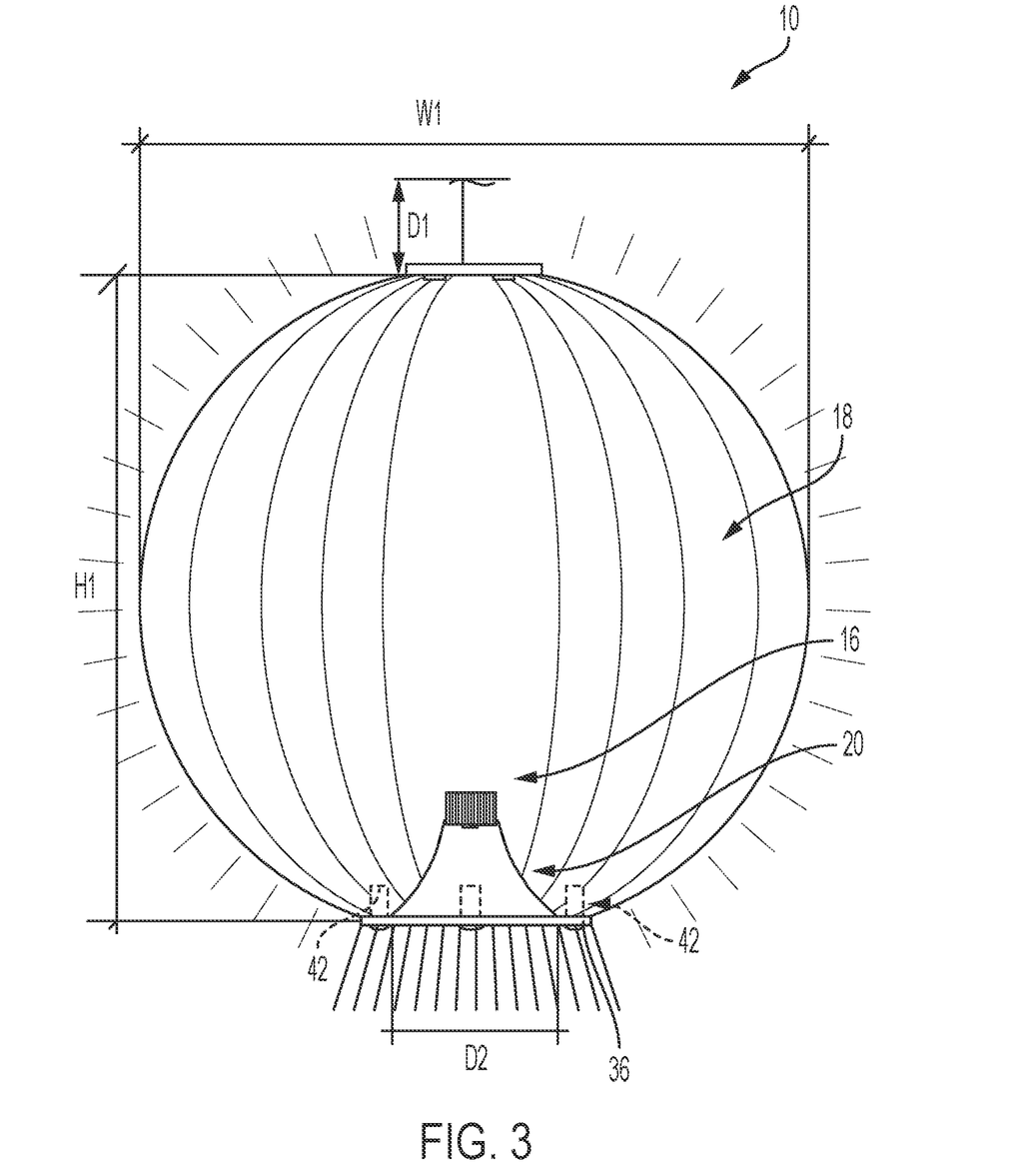
FIG. 3 is a side elevational view of an exemplary luminaire according to an embodiment of the present technology.

As shown in FIG. 3, the luminaire 10, in some embodiments, includes at least one occupancy sensor 42 that is configured to detect occupants in a predetermined area surrounding the luminaire 10 and generate occupancy data. The occupancy sensor 42 communicates the occupancy data to the controller 38 which, upon receiving the occupancy data, determines whether to activate or deactivate the luminaire 10. For example, if the occupancy sensor 42 detects that a person has entered the area surrounding the luminaire 10, then the controller 38 generates and communicates an activation control signal to the first driver 22 and the second driver 24 to activate the ambient light source 14 and the downlight light source 16. Likewise, if the occupancy sensor 42 detects that all occupants have vacated the area surrounding the luminaire 10, then the controller 38 generates and communicates a deactivation control signal to the first driver 22 and the second driver 24 to deactivate the ambient light source 14 and the downlight light source 16. Preferably, the controller 38 couples the activation control signal with the illuminance mode control signal determined by the time-of-day data to ensure the appropriate illuminance mode is activated by an occupant's presence near the luminaire 10. In some embodiments, the occupancy sensor 42 is positioned adjacent the aperture 36 of the frame 12, as shown in FIG. 3. In some embodiments, the luminaire 10 includes four occupancy sensors 42 surrounding the aperture 36, however the present technology is not limited thereto and contemplates the luminaire 10 having more or less than four occupancy sensors 42 in various positions along the frame 12.

In some embodiments, the luminaire 10 includes a mounting means for mounting the luminaire 10 to an electrical junction box in a ceiling above, for example, a table, or other commonly used seating area in the home, to provide adequate light levels for circadian effect to occupants in the area surrounding the luminaire 10. In some embodiments, the mounting means include a wire or cable 44 connected to the first end 12A of the frame 12 via a wire grip 46, as shown in FIG. 2. A plug-in format is used in some embodiments that is suspended from a hook in the ceiling with the power cord supporting the luminaire as is common for residential pendant lamps when no ceiling junction box is available. The luminaire 10 has a height H1, a width W1, and a suspension depth D1 measured from the ceiling to the first end 12A of the frame 12, as shown in FIG. 3. In some embodiments, the height H1 is about 750 mm, the width W1 is about 750 mm, and the suspension depth D1 is about 250 mm to about 300 mm, such that the luminaire 10 has a total length of about 1000 to about 1050 mm. In some embodiments, the aperture 36 has a diameter D2 of about 100 mm. The luminaire has a mounting height H2 measured from the second end 12B of the frame 12 to a surface that the luminaire 10 is mounted above, such as a table, as shown in FIG. 5. In some embodiments, the mounting height H2 is about 600 to about 750 mm. However, the present technology is not limited thereto and contemplates embodiments having different dimensions.

Figure 9:
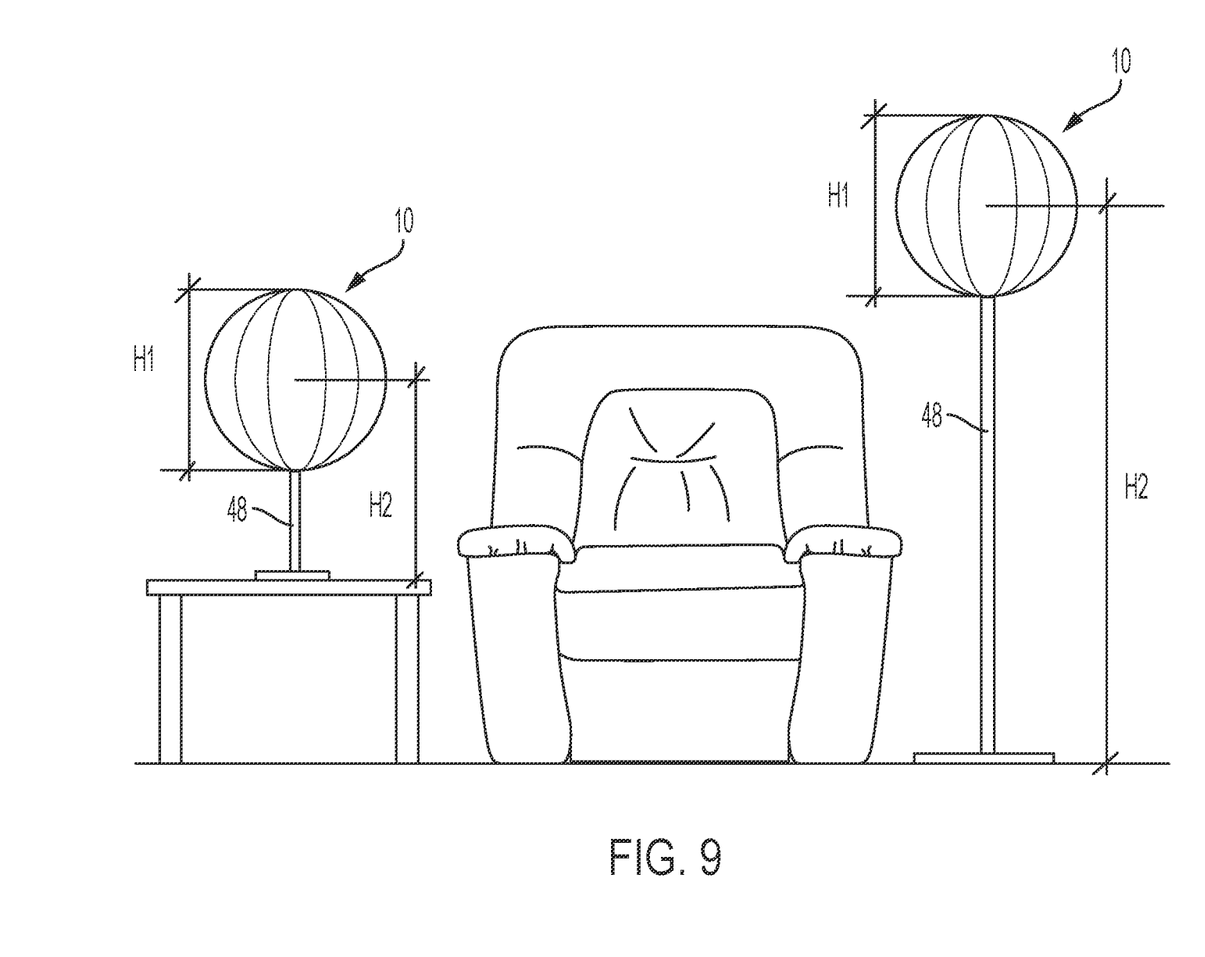
FIG. 9 is a side elevational view of exemplary freestanding luminaires according to an embodiment of the present technology.

In some embodiments, the luminaire 10 includes a stand 48 for use as a lamp, such as a table-mounted lamp or a free-standing floor lamp, as shown in FIG. 9. Such lamp embodiments permit more flexibility for users to install one or more luminaires 10 in a desired area when ceiling-mounted options are not feasible or desirable. Such lamp embodiments are smaller in scale but still retain the low-glare appearance and include the same functionality and onboard technology as the ceiling-mounted embodiments discussed above. For example, in some embodiments the luminaire 10 has a height H1 of about 400 mm and the stand 48 has a height H2, which is about 600 mm for some table lamp embodiments and about 1.4 m for some floor lamp embodiments. However, the present technology is not limited thereto and contemplates embodiments having different dimensions.

Accordingly, the advantages of the luminaire according to some embodiments of the present technology are that they deliver equally effective circadian stimulation as luminaires solely dedicated to that purpose, but in an aesthetically pleasing manner with little to no discomfort glare. Additionally, some embodiments have onboard technology making it capable of delivering the right stimulus at the right time of day without the user of the product having to concern him- or herself with programming a schedule. Beyond providing a high circadian stimulus during the daytime, some embodiments of the luminaire continue to provide pleasing, comfortable, and functional lighting during the evening time while ensuring the amount of light reaching the eyes of occupants is below the threshold for circadian disruption at night. In addition to being beneficial for end users in search of an at-home lighting product that is of both high design quality and circadian impact, some embodiments of the luminaire have the added advantage of being a tool for researchers investigating the effect of circadian stimulation in residential environments by being configured to collect and log occupancy, light exposure, and energy data via the on-board sensors and control systems.

Although the technology has been described and illustrated with respect to exemplary embodiments thereof, it should be understood by those skilled in the art that the foregoing and various other changes, omissions, and additions may be made therein and thereto, without parting from the spirit and scope of the present technology.

What is claimed is:

1. A luminaire comprising:
   a frame comprising a first end, a second end opposite the first end, and an aperture at the second end;
   an ambient light source positioned within the frame adjacent the first end of the frame;
   a downlight light source positioned within the frame adjacent the second end of the frame;
   a diffuser connected to the frame and at least partially surrounding the ambient light source; and
   a reflector positioned within the aperture of the frame, the reflector configured to direct light emitted by the downlight light source.

2. The luminaire of claim 1, further comprising:
   a first driver in electrical communication with the ambient light source, the first driver is configured to adjust the illuminance of the ambient light source;
   a second driver in electrical communication with the downlight light source, the second driver is configured to adjust the illuminance of the downlight light source; and
   a controller in electrical communication with the first driver and the second driver, the controller is configured to send control signals to the first driver and the second driver to change the ambient light source and the downlight light source between a plurality of illuminance modes.

3. The luminaire of claim 2, wherein the plurality of illuminance modes comprises a circadian effective mode and a circadian ineffective mode.

4. The luminaire of claim 3, wherein when operating in the circadian effective mode, the luminaire provides a circadian stimulus of at least 0.3, the illuminance of the ambient light source is at least 350 Lux, and the illuminance of the downlight light source is at least 300 Lux.

5. The luminaire of claim 3, wherein when operating in the circadian ineffective mode, the luminaire provides a circadian stimulus of no more than 0.1, the illuminance of the ambient light source is no more than 50 Lux, and the illuminance of the downlight light source is at least 300 Lux.

6. The luminaire of claim 3, wherein the controller is programmable and the luminaire further comprises a timeclock such that the controller automatically changes the luminaire between the circadian effective mode and the circadian ineffective mode at predetermined times.

7. The luminaire of claim 3, wherein the plurality of illuminance modes further comprises an ambient-only mode and a downlight-only mode.

8. The luminaire of claim 2, further comprising at least one occupancy sensor in communication with the controller, the at least one occupancy sensor is configured to detect occupants in a predetermined area near the luminaire and communicate occupancy data to the controller which, upon receiving the occupancy data, is configured to activate or deactivate the luminaire.

9. The luminaire of claim 1, wherein the ambient light source comprises at least one LED source and at least one lens, the at least one lens having approximately a 340-degree light distribution pattern.

10. The luminaire of claim 9, wherein the ambient light source has a Lambertian light distribution pattern.

11. The luminaire of claim 9, wherein the at least one LED source comprises a plurality of concentric annular LED boards.

12. The luminaire of claim 1, wherein the downlight light source comprises an LED chip-on-board.

13. The luminaire of claim 1, wherein the reflector is shaped such that the downlight light source has an asymmetric light distribution pattern, the asymmetric light distribution pattern comprising an approximately 60-degree by approximately 110-degree pattern.

14. The luminaire of claim 1, wherein the frame comprises a plurality of perimeter members connecting the first end of the frame to the second end of the frame; and
   the diffuser comprises a plurality of panels, each of the plurality of panels is connected to and positioned between adjacent perimeter members of the frame.

15. The luminaire of claim 14, wherein each of the plurality of perimeter members is curved such that the frame has a generally spherical shape.

16. A method of promoting circadian entrainment to an area, comprising:
   providing a lighting system comprising a luminaire and a controller in electrical communication with the luminaire, the luminaire comprising:
      a frame comprising a first end, a second end opposite the first end, and an aperture at the second end;
      an ambient light source positioned within the frame adjacent the first end of the frame;
      a downlight light source positioned within the frame adjacent the second end of the frame;
      a first driver in electrical communication with the ambient light source and the controller, the first driver is configured to adjust the illuminance of the ambient light source;
      a second driver in electrical communication with the downlight light source and the controller, the second driver is configured to adjust the illuminance of the downlight light source;
      a timeclock in electrical communication with the controller;
      a diffuser connected to the frame and at least partially surrounding the ambient light source; and
      a reflector positioned within the aperture of the frame, the reflector configured to direct light emitted by the downlight light source;
   generating, via the timeclock, time of day data;
   communicating the time of day data to the controller;
   generating, via the controller, at least one illuminance mode control signal in response to the time of day data;
   communicating the at least one illuminance mode control signal to at least one of the first driver and the second driver; and
   adjusting the illuminance of at least one of the ambient light source and the downlight light source between a plurality of illuminance modes in response to the at least one illuminance mode control signal.

17. The method of claim 16, wherein the plurality of illuminance modes comprises a circadian effective mode and a circadian ineffective mode.

18. The method of claim 17, wherein when operating in the circadian effective mode, the luminaire provides a circadian stimulus of at least 0.3, the illuminance of the ambient light source is at least 350 Lux, and the illuminance of the downlight light source is at least 300 Lux.

19. The method of claim 17, wherein when operating in the circadian ineffective mode, the luminaire provides a circadian stimulus of no more than 0.1, the illuminance of the ambient light source is no more than 50 Lux, and the illuminance of the downlight light source is at least 300 Lux.

20. The method of claim 16, further comprising:
detecting, via at least one occupancy sensor of the luminaire, occupants in a predetermined area near the luminaire;
generating occupancy data;
communicating the occupancy data to the controller;
generating, via the controller, at least one of an activation or a deactivation control signal in response to the occupancy data;
communicating the at least one of the activation or deactivation control signal to the first driver and the second driver; and
adjusting the illuminance of the ambient light source and the downlight light source in response to the at least one of the activation or deactivation control signal.

* * * * *